US00PP25348P3

(12) United States Plant Patent
Skelton

(10) Patent No.: US PP25,348 P3
(45) Date of Patent: Mar. 17, 2015

(54) *ACTINIDIA CHINENSIS* PLANT NAMED 'B52'

(50) Latin Name: *Actinidia chinensis*
Varietal Denomination: B52

(71) Applicant: Donald Alfred Skelton, Huntly (NZ)

(72) Inventor: Donald Alfred Skelton, Huntly (NZ)

( * ) Notice: Subject to any disclaimer, the term of this patent is extended or adjusted under 35 U.S.C. 154(b) by 42 days.

(21) Appl. No.: 13/986,592

(22) Filed: May 15, 2013

(65) Prior Publication Data

US 2014/0345009 P1 Nov. 20, 2014

(51) Int. Cl.
*A01H 5/00* (2006.01)

(52) U.S. Cl.
USPC ..... Plt./156

(58) Field of Classification Search
USPC ..... Plt./156
See application file for complete search history.

*Primary Examiner* — Kent L Bell
(74) *Attorney, Agent, or Firm* — Cassandra Bright

(57) ABSTRACT

A new and distinct *Actinidia chinensis* cultivar named 'B52' is disclosed, characterized by having distinctive pale yellow flesh fruit, and a mid seasonal harvest time. Additionally, the new variety produces oblong fruit with weak skin adherence to flesh and with a distinctive flat, stylar end shape. The new variety is suitable for commercial production of kiwi fruit.

3 Drawing Sheets

Latin name of the genus and species: *Actinidia chinensis*.
Variety denomination: 'B52'.

BACKGROUND OF THE INVENTION

The new cultivar is a product of a planned breeding program under the direction of the inventor, Donald Alfred Skelton, a citizen of New Zealand. The seed parent is the unpatented, proprietary variety referred to as *Actinidia chinensis* 'B361'. The pollen parent is the unpatented, proprietary seedling variety referred to as *Actinidia chinensis* 'A28'.

Fruit of the new variety was first evaluated in 2001 with favorable results. After the first evaluation, semi-hardwood cuttings were made of 'B52' and were grafted onto seedling rootstocks of *A. deliciosa*. Evaluation, asexual propagation and grafting all first took place at a research nursery in North Waikato, New Zealand. Subsequent evaluations of the variety have shown the characteristics to be true to type.

SUMMARY OF THE INVENTION

The cultivar 'B52' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'B52' These characteristics in combination distinguish 'B52' as a new and distinct *Actinidia chinensis* cultivar:

1. Oblong shaped fruit form
2. Heavy fruit weight, similar to the known variety 'Hayward'.
3. Flat stylar fruit end.
4. Pale yellow flesh fruit
5. Mid season fruit harvest
6. Weak adherence of fruit skin to flesh
7. Weak adherence of hair to fruit skin

COMMERCIAL COMPARISON

The new variety is best compared to the commercial variety, 'Hort16A', U.S. Plant Pat. No. 11,066. 'B52' is similar to 'Hort16A' in many horticultural characteristics, however, 'B52' produces mature fruit approximately 2 weeks earlier in the season than 'Hort16A'. Additionally, fruit of the new variety 'B52' has a flat stylar end, compared to the strongly protruding stylar end of 'Hort16A'. Fruit differences can also be noted in the weight. Fruit produced by plants of 'B52' are heavier than fruits produced by 'Hort16A'.

The new variety is similar to the seed parent variety in some horticultural characteristics. However, the new variety differs in the following;

1. The new variety has a late-season bud set, compared to the mid-season bud set of the seed parent.
2. The new variety flowers later than the seed parent variety.
3. Fruit of the new variety ripens later than fruit of the seed parent variety.

The new variety can be compared to the pollen parent variety, however, the plants clearly differ, as the new variety is a fruit producing female plant and the pollen parent is a non-fruiting male plant. Additionally, the new variety differs in the following;

1. The new variety has a late-season bud set, compared to the early-season bud set of the pollen parent.
2. The new variety flowers later than the pollen parent variety.
3. No fruit is produced by the pollen parent.

BRIEF DESCRIPTION OF THE PHOTOGRAPH

The accompanying photograph in FIG. 1 illustrates in full color examples of typical flowers of 'B52'.

Figure 1:
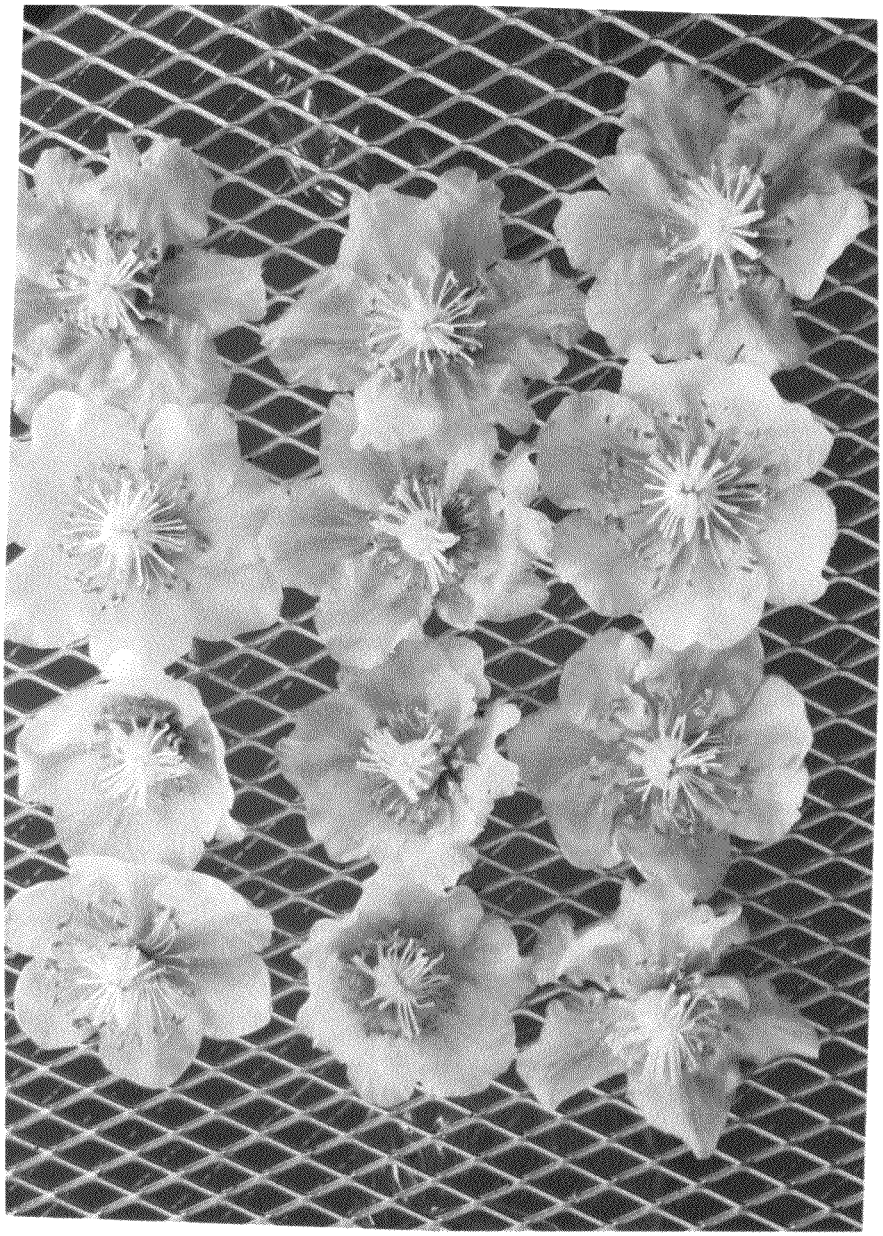
Figure 2:
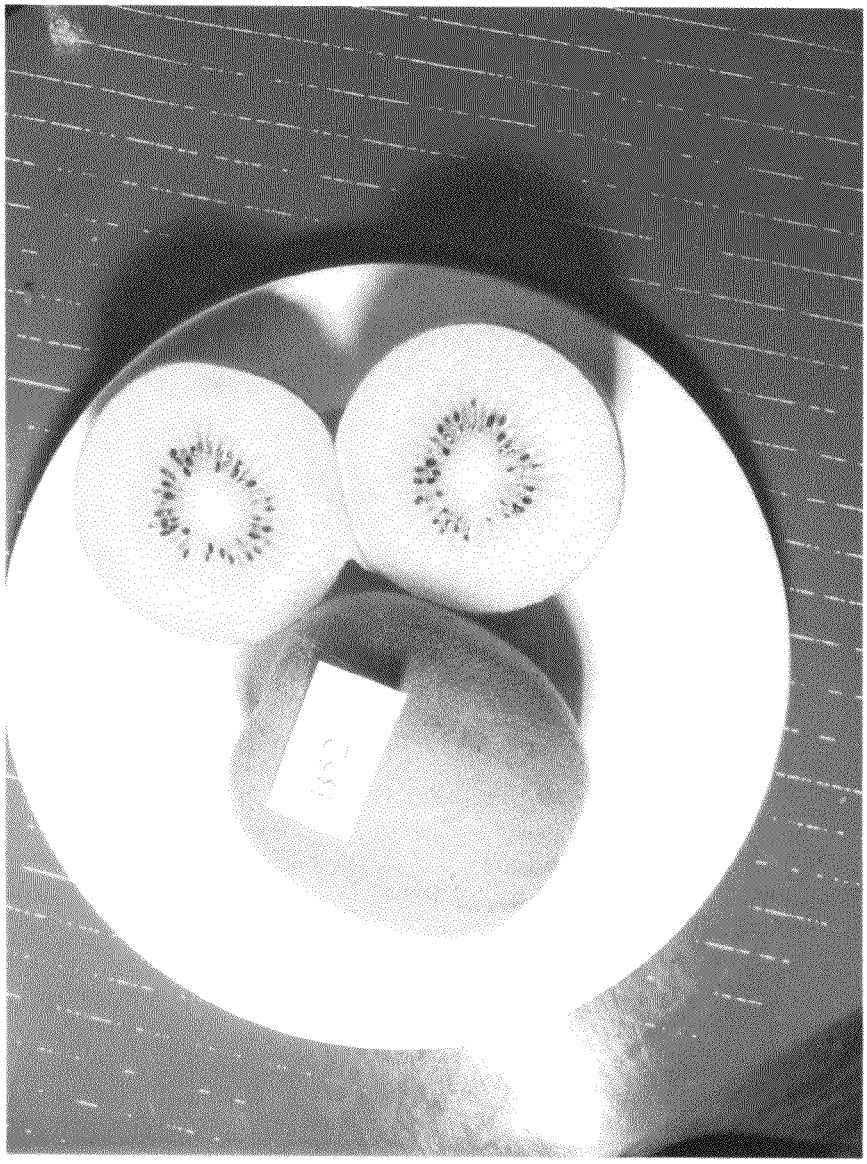
FIG. 2 illustrates fruit harvested from 'B52'.
Figure 3:
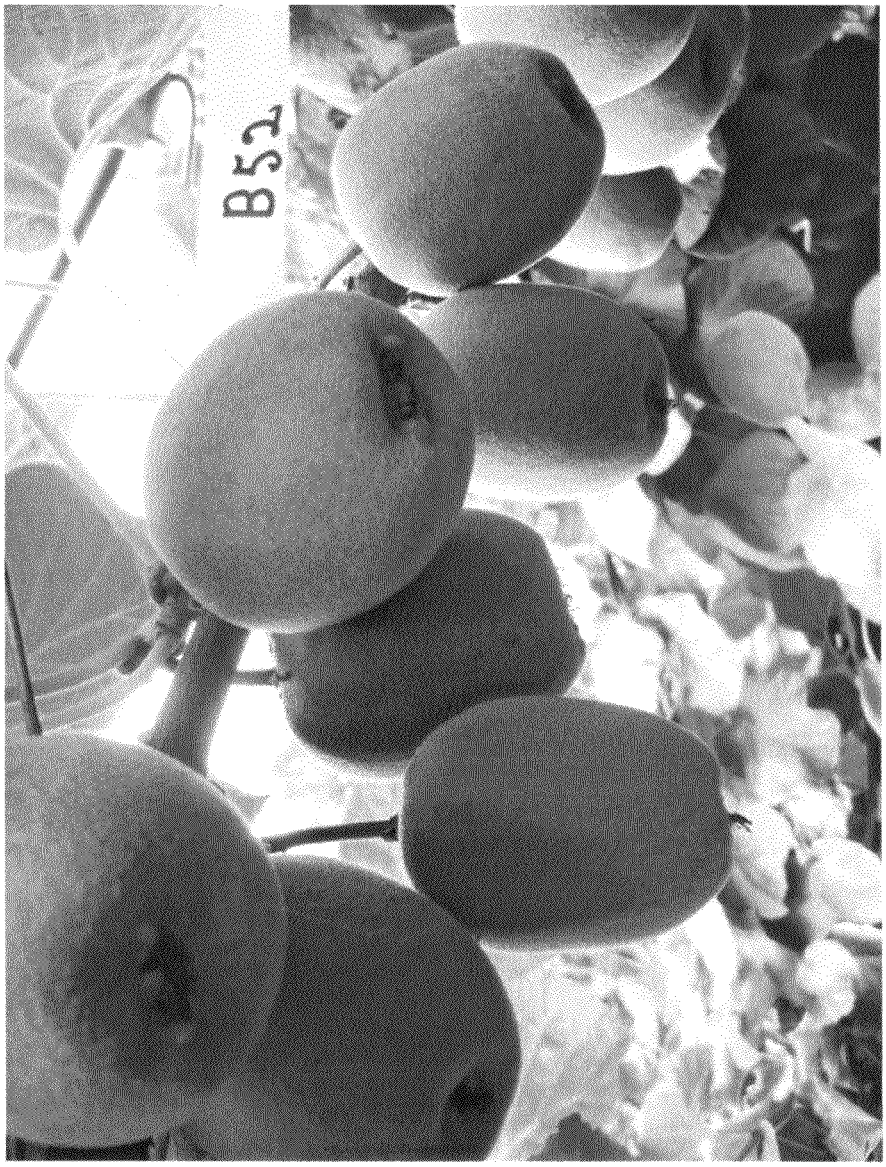
FIG. 3 illustrates in full color typical foliage, hanging fruit and stems on plants of 'B52'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'B52' plants grown outdoors under commercial trial conditions in North Waikato, New Zealand. The growing temperature ranged from 10° C. to 30° C. during the day and −4° C. to 18° C. at night. Annual rainfall is approximately 125 cm per year. Measurements and numerical values represent an average of 10 typical plant types.

Botanical classification: *Actinidia chinensis* 'B52'.

PROPAGATION

'B52' can be successfully grafted onto rootstocks of *Actinidia deliciosa.*

PLANT

*Age of the plant described.*—Approximately 5 years.
*Sex expression.*—Female.
*Ploidy.*—Diploid.
*Average height.*—180 cm.
*Average width.*—Canopy is an average of 300 cm by 400 cm to 500 cm by 500 cm.
*Vigor.*—Moderate.
*Young shoot color.*—Near RHS Yellow-Green N144B.
*Young shoot texture.*—Mainly glabrous, with some light scaliness.
*Trunk diameter.*—Approximately 3.75 cm for a 6 year old vine.

Stem characteristics:
*Color.*—Between RHS Brown 200D and Greyed-Purple 187A on upper (sunny side) surface.
*Lower surface.*—Grey-Brown 199A.
*Stem diameter.*—Average 1.5 cm.
*Stem length.*—Average range 100 to 200 cm.
*Stem texture.*—Moderately rough, non-pubescent with a moderate amount of very medium sized lenticels.
*Lenticel description.*—Length: Average 0.4 cm. Width: Average 0.15 cm. Density: Approximately 30 per 5 cm of stem.
*Stem pith.*—Solid.
*Leaf scar description.*—Flat.

FOLIAGE

Leaf:
*Average length.*—16 cm.
*Average width.*—18 cm.
*Shape of blade.*—Obovate.
*Apex.*—Retuse.
*Base.*—Cordate, basal lobes not touching.
*Attachment.*—Petioled.
*Margin.*—Moderately ciliate.
*Texture of top surface.*—Very slightly puckered. Non-pubescent.
*Texture of under side.*—Sparsely pubescent.
*Color.*—Mature foliage upper side: Near RHS Green 137A. Mature foliage under side: Near RHS Green 138C.
*Petiole.*—Length: Average length 17.5 cm. Diameter: Approximately 0.4 cm. Texture: Glabrous. Pubescence: None. Color: Upper Surface near RHS Yellow-Green N143D. Moderate anthocyanin on upper side only, near Greyed-Purple 187C.

FLOWER

*Flowers per inflorescence.*—Normally 1, occasionally 3.
*Bud color.*—Near RHS Yellow-Green 145A.
*Bud shape.*—Oblong.
*Bud break.*—Mid season.
*First flower.*—Mid season Pollinized by proprietary varieties referred to as 'A55', 'CMWW85' and 'CMW53'.
*Diameter.*—Average 6 cm.
*Depth.*—Average 4.1 cm.
*Petal quantity.*—6 to 10 per flower.
*Petals overlapping.*—Yes.

Petals:
*Length.*—Approximately 2.9 cm.
*Width.*—Approximately 1.7 cm.
*Shape.*—Spatulate.
*Aspect.*—Slightly undulating.
*Margin.*—Entire, with infrequent irregular shallow crenations.
*Texture.*—Glabrous, all surfaces.
*Base.*—Attenuate.
*Apex.*—Obtuse or retuse.
*Petal color.*—Near RHS White 155A upper and lower surfaces.
*Filament color.*—Near RHS White 157A.
*Anther color.*—Near RHS Yellow-Orange 16A.
*Attitude of styles.*—Semi-erect.
*Style color.*—Near RHS White 155A.
*Style quantity.*—Average 20.
*Hair on ovary.*—Dense.
*Color of ovary.*—Near RHS White 155A.
*Number of sepals.*—6 to 10.
*Color of sepals.*—Near RHS Green 144B upper and lower surfaces.
*Sepal width.*—Approximately 1 cm.
*Sepal length.*—Approximately 1.3 cm.
*Sepal texture.*—Smooth.
*Sepal shape.*—Deltate.
*Sepal margin.*—Entire.
*Sepal apex.*—Acute.
*Sepal base.*—Truncate.

Peduncle:
*Length.*—Average 6.6 cm.
*Diameter.*—Average 0.5 cm.
*Color.*—Near RHS Green 144B.
*Texture.*—Smooth.

FRUIT

*Average weight.*—121 grams.
*Average length.*—7.5 cm.
*Average diameter.*—5.1 cm.
*Color outer pericarp.*—Near RHS Yellow 2D.
*Color inner pericarp.*—Near RHS Yellow 2A.

*Core color*.—Near RHS Yellow 2B.
*Core diameter*.—Average 0.7 cm.
*General shape*.—Oblong.
*Median cross section*.—Circular.
*Stylar end shape*.—Flat.
*Shoulder shape*.—Squared, truncate.
*Calyx ring*.—Present.
*Calyx ring expression*.—Moderate.
*Skin color at harvest*.—Near RHS Yellow-Green 152C.
*Hair on fruit skin*.—Downy.
*Hair adherence to skin*.—Weak.
*Skin adherence to flesh at maturity*.—Weak.
*Fruit core shape*.—Transversely elliptic.
*Core-woody spike*.—Small.
*Lenticels on fruit*.—Weak expression of lenticels on fruit.
*Locules*.—Quantity per fruit: 27 to 29. Length: Variable, a typical range is 1.5 cm to 2.3 cm. Width: Highly variable, no typical range. Color: Near RHS Yellow 2A.
*Mature seed color*.—Black.
*Dried seed*.—Brown.
*Harvest time*.—Very early season.
Fruit stem:
*Length*.—Average range 3.1 cm to 8.0 cm.
*Diameter*.—Average 0.5 cm.
*Color*.—Near RHS Greyed-Orange 165C.
*Texture*.—Smooth.

OTHER CHARACTERISTICS

Storage life: Storage life is a minimum of 3 months at 2° C.
Disease/pest resistance: Neither resistance nor susceptibility to pathogens and pests common to *Actinidia chinensis* have been observed.
Temperature tolerance: Tolerates low temperatures to approximately −5° C. without negative effects, tolerates high temperatures to approximately 35° C. without negative effects.

What is claimed is:

1. A new and distinct cultivar of *Actinidia chinensis* plant named 'B52' as herein illustrated and described.

* * * * *